United States Patent [19]

Anthony

[11] 4,412,532
[45] Nov. 1, 1983

[54] EYELASH RETRACTOR

[76] Inventor: Richard R. Anthony, 304 West Union St., Morganton, N.C. 28655

[21] Appl. No.: 332,617

[22] Filed: Dec. 21, 1981

[51] Int. Cl.³ .................................... A61B 17/02
[52] U.S. Cl. ................................. 128/20; 128/341
[58] Field of Search .............. 128/20, 303 R, 76.5, 128/341, 345–346

[56] References Cited

U.S. PATENT DOCUMENTS

| | | | |
|---|---|---|---|
| 1,230,873 | 6/1917 | Crossley | 128/20 |
| 1,375,445 | 4/1921 | Crossley | 128/20 |
| 1,810,466 | 6/1931 | Deutsch | 128/20 |
| 2,438,646 | 3/1948 | Pulliam | 128/20 |
| 2,702,540 | 2/1955 | Debeh | 128/20 |
| 2,845,925 | 8/1958 | Jayle | 128/20 |
| 3,054,398 | 9/1962 | Kobler | 128/20 |
| 3,522,800 | 8/1970 | Lesser | 128/20 |
| 3,782,370 | 1/1974 | McDonald | 128/20 |
| 4,037,589 | 7/1977 | McReynolds | 128/20 |
| 4,190,042 | 2/1980 | Sinnreich | 128/20 |

Primary Examiner—Lee S. Cohen
Assistant Examiner—Angela D. Sykes
Attorney, Agent, or Firm—Bell, Seltzer, Park & Gibson

[57] ABSTRACT

The eyelash retractor covers and shields the eyelashes and adjacent portions of the eyelid during examination of and/or surgery on the eyeball of a patient and comprises a body member of thin film material with a hooked inner portion adapted to extend beneath the eyelid of the patient with the portion of the body member adjacent the hooked portion covering and shielding the eyelashes and substantially the full width of the adjacent portion of the eyelid to maintain the eyelashes out of the area of the eyeball and provide a clear and unobstructed field for examination of and/or surgery on the eyeball. The eyelash retractor is disclosed as being divided intermediate the opposite sides to form two separate parts with mating free inner sides adapted to mate in abutting or overlapping relationship when the retractor parts are positioned on the eyelid of the patient. The eyelash retractor is simple to apply and remove and is sufficiently low in cost that it may be discarded after one use.

7 Claims, 6 Drawing Figures

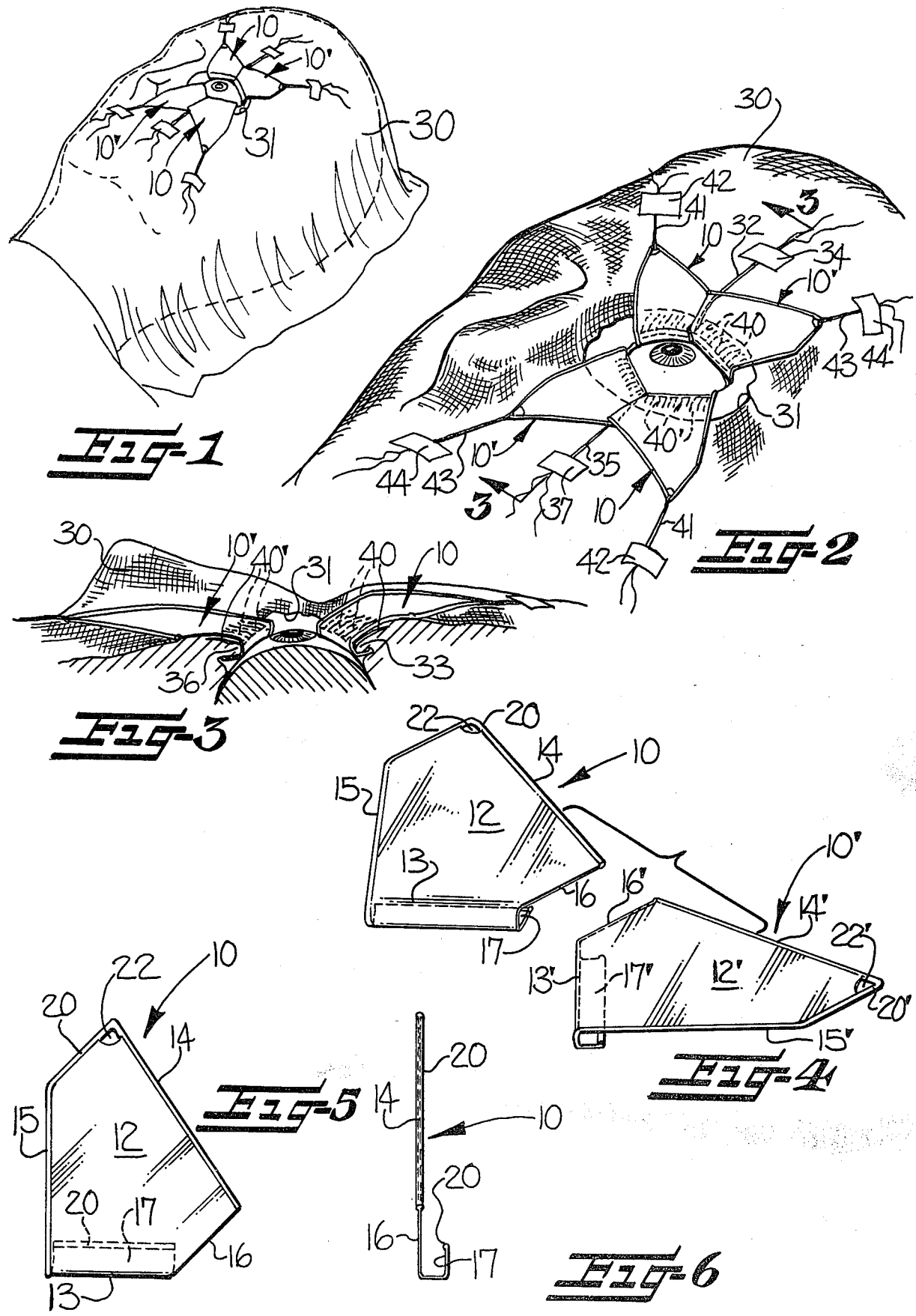

EYELASH RETRACTOR

FIELD OF THE INVENTION

This invention relates to an eyelash retractor for covering and shielding the eyelashes and to maintain the eyelashes out of the area of the eyeball in order to provide a clear and unobstructed field for examination of and/or surgery on the eyeball.

BACKGROUND OF THE INVENTION

During examination of and/or surgery on the eyeball, the eyelids are normally maintained in an open or retracted position by eyelid retracting devices which normally include hooked members adapted to engage and retract the eyelids. Typical examples of such known types of eyelid retractors are disclosed in U.S. Pat. Nos. 1,230,873; 1,375,445; 2,438,646 and 2,702,540. It is also known to retract the eyelid by utilizing a "bridle" suture which involves inserting a suture thread through the eyelid and securing the ends of the suture at a remote location to maintain the eyelids in a retracted position. A special frame is disclosed in U.S. Pat. No. 2,845,925 for securing the outermost ends of the suture thread when the eyelids are retracted by suture threads.

While the eyelids are retained in retracted condition by the above-described known eyelid retracting devices or by use of the bridle suture, such eyelid retracting devices and the bridle suture do not fully cover and shield the eyelashes, and thus the eyelashes may interfere with the examination of and/or surgery on the eyeball. To eliminate any obstruction by the eyelashes during the examination of and/or surgery on the eyeball, it is presently the common practice to cut or trim the eyelashes from the eyelids of the patient. This practice is tedious and time consuming and leaves the patient without eyelashes until new eyelashes can be grown. Also, the cut eyelashes may be deposited in the eye and additional time is consumed in removing the same.

It is also recognized that during surgical procedures of the eye, there is a risk of bacterial contamination from the adjacent lid skin surface and lid mucous membrane surface, and the present lid retracting techniques do not fully avoid this risk.

SUMMARY OF THE INVENTION

With the foregoing in mind, it is an object of the present invention to provide an eyelash retractor which extends along substantially the full width of the eyelid and covers and shields the eyelashes and adjacent portion of the eyelid so as to maintain the eyelashes out of the area of the eyeball and to provide a clear and unobstructed field for examination of and/or surgery on the eyeball.

It is a further object of the present invention to provide an eyelash retractor which effectively covers the eyelashes and lid margins to protect from bacterial contamination.

The eyelash retractor of the present invention is preferably molded of an inexpensive plastic material so that the cost of producing the same is reduced to the point that the eyelash retractor may be considered disposable, that is, the eyelash retractor may be discarded after one use. The present eyelash retractor is primarily formed of thin flexible film material with an enlarged reinforcing or stiffening rim surrounding the outer periphery so that the general shape of the retractor is retained while the thin flexible film portion can easily conform to the shape of the retracted eyelid, and the eyelash retractor can be used with the conventional eyelid retractor or with the usual bridle suture.

The present eyelash retractor includes a body member of thin film material with an enlarged rim connected to and extending around the outer periphery thereof, and a hooked portion extends along the inner edge of the body member. The hooked portion includes a lip extending substantially parallel to and spaced from the adjacent portion of the body member. The lip is adapted to extend beneath the eyelid of the patient with the portion of the body member adjacent the hooked portion covering and shielding the eyelashes and adjacent portion of the eyelid to maintain the eyelashes out of the area of the eyeball and provide a clear and unobstructed sterile field surrounding the eyeball. The eyelash retractor is illustrated and described as being of a two-piece construction to facilitate insertion and removal of the eyelash retractor and for accurately conforming to the configuration of the retracted eyelid. However, it is to be understood that the present eyelash retractor could be molded or otherwise formed in a single piece, if desired.

The present eyelash retractor is divided intermediate the opposite sides to form two separate parts with one part being the mirror image of the other part. Each part is provided with an inner free side adapted to mate in abutting or overlapping relationship when both parts of the eyelash retractor are positioned on the eyelid of the patient. The inner edge of the retractor defines a substantially V-shaped configuration with straight sides joining at a vertex positioned in the center of the inner edge and at the mating free sides. The outer edge also defines a shallow V-shaped configuration with straight edges joining at a vertex positioned in the center of the outer edge and at the mating free sides. Openings are provided in the thin film material at the juncture of the opposed sides and the outer edge to receive a suture thread for holding the eyelash retractor in position.

BRIEF DESCRIPTION OF THE DRAWINGS

Other objects and advantages will appear as the description proceeds when taken in connection with the accompanying drawings, in which FIG. 1 is a perspective view of the head of a patient and illustrating the present eyelash retractor in position on both the upper and lower eyelids of the patient;

FIG. 2 is an enlarged perspective view of a fragmentary portion of the exposed eye of the patient shown in FIG. 1 and showing the eyelash retractor positioned on both the upper and lower eyelids;

FIG. 3 is a somewhat schematic vertical sectional view taken substantially along the line 3—3 in FIG. 2;

FIG. 4 is a perspective view of the two parts of the eyelash retractor, removed from the patient;

FIG. 5 is a front elevational view of one part of the eyelash retractor; and

FIG. 6 is a side elevational view of the eyelash retractor, looking at the right-hand side of FIG. 5.

DESCRIPTION OF THE ILLUSTRATED EMBODIMENT

As illustrated in FIGS. 1-4, the present eyelash retractor is illustrated as being divided intermediate opposite sides to form two separate parts, broadly indicated at 10 and 10', with the part 10' being a mirror image of the part 10. The components of the part 10 will be described in detail, with particular reference to FIGS. 5 and 6, and the corresponding components of the part 10' will bear the same reference characters with the prime notation added.

The part 10 includes a body member 12 of thin and flexible plastic film material including an inner edge 13, an outer edge 14, an opposed or outer side 15, and a mating free inner side 16. A hooked portion extends along the inner edge 13 and includes a lip 17 extending substantially parallel to and spaced from the adjacent portion of the body member 12. An enlarged rim 20 is connected to and extends around the periphery of the body member 12 and along the free edge of the lip 17 but does not extend along the mating free inner side 16. The enlarged rim 20 serves as reinforcement or stiffening to aid in retaining the general shape of the retractor while permitting the thin and flexible body portion 12 to conform to the retracted eyelid and adjacent area. The body member 12 is provided with an opening 22 at the juncture of the outer edge 14 and the opposed or outer side 15 for receiving a suture or thread to anchor or fix the eyelash retractor, in a manner to be presently described.

To use the eyelash retractor of the present invention during the examination of and/or surgery on the eyeball of a patient, the face and head of the patient is first covered by a suitable surgical drape 30 which is secured in position in the usual manner and an opening 31 is cut in the surgical drape 30 to provide access to the eye to be operated upon. A bridle suture 32 is then inserted about the midpoint of the upper eyelid 33 and the eyelid is retracted and the suture 32 is secured to the surgical drape 30, by any suitable means such as a piece of tape 34. A bridle suture 35 is then inserted about the midpoint of the lower eyelid 36 and is secured to the surgical drape 30 by a tape 37 to hold the lower eyelid in retracted condition.

The hooked portion of the inner edge 13 of the part 10 is then positioned over the inner half of the retracted upper eyelid 33 so that the lip 17 extends beneath the eyelid and the adjacent portion of the body member 12 covers and shields the eyelashes 40 on the inner half of the upper eyelid 33. A suitable suture thread 41 is passed through the opening 22 and secured to the surgical drape 30, as by a tape 42, to retain the part 10 in position covering the eyelashes 40 on the inner portion of the eyelid 33. The other part 10' is then positioned to cover the outer portion of the upper eyelid 33 and cover and shield the eyelashes with the lip 17' being positioned beneath the outer portion of the upper eyelid 33. The retractor part 10' is maintained in position by a suture thread 43 and tape 44 and with the mating free inner side 16' being positioned in overlapping or abutting relationship with the mating free inner side 16 of the part 10.

The parts 10 and 10' of the eyelash retractor are then positioned in the same manner on the lower eyelid 36 to cover and shield the eyelashes 40' and maintain them out of the field of the eyeball to provide a clear and unobstructed field for examination of and/or surgery on the eyeball. If desired, the position of the eyeball may be fixed by the use of additional bridle sutures, not shown.

As clearly illustrated in FIG. 2, the eyelash retractor of the present invention extends along substantially the full width of the eyelid and covers and shields the eyelashes without the necessity of cutting or trimming the eyelashes prior to examination of and/or surgery on the eyeball. When the two parts 10 and 10' are positioned as shown in FIG. 2, the eyelash retractor includes an inner edge which defines a substantially V-shaped configuration with straight sides (the inner edges 13, 13') joining at a vertex positioned in the center of the inner edge of the eyelash retractor. Also, the eyelash retractor is provided with an outer edge which defines a V-shaped configuration with straight sides (defined by the outer edges 14, 14') joining at a vertex positioned in the center of the upper edge of the eyelash retractor.

It is to be understood that the parts 10, 10' of the present eyelash retractor may be provided in several different sizes to accommodate patients with different sizes of eyes and eyelids, for example adults, children and infants. The specific configuration of the eyelash retractor parts, as illustrated in FIG. 5, may be varied, if desired. As an illustrative and nonlimiting example, the part 10 shown in FIG. 5 has the inner edge 13 joined to the mating free inner side 16 at an included obtuse angle of 135 degrees. The mating free inner side 16 joins the outer edge 14 at an angle of 100 degrees while the inner edge 13 joins the opposed or outer side 15 at a 90-degree angle. The opposed or outer side 15 includes an obtuse angle of 135 degrees and is joined to the outer edge 14 at an angle of 80 degrees. The mating inner side 16 is 10 millimeters in length, the outer edge 14 is 25 millimeters, the inner edge 13 is 14 millimeters, the inner portion of the opposed or outer side 15 is 20 millimeters, and the outer portion of the opposed or outer side 15 is 11 millimeters.

The present eyelash retractor provides a simple and inexpensive device for covering and shielding the eyelashes and adjacent portion of the eyelids during examination of and/or surgery on the eyeball of a patient. The eyelash retractor can be easily applied and removed and maintains the eyelashes out of the area of the eyeball without requiring cutting and trimming of the eyelashes.

In the drawings and specification there has been set forth the best mode presently contemplated for the practice of the present invention, and although specific terms are employed, they are used in a generic and descriptive sense only and not for purposes of limitation, the scope of the invention being defined in the claims.

That which is claimed is:

1. An eyelash retractor for covering and shielding the eyelashes and adjacent portion of the eyelid during the examination of and/or surgery on the eyeball of a patient, said eyelash retractor comprising two separate body members of thin film material including inner and outer edges and opposed sides, a hooked portion extending along the full length of said inner edge of each of said body members and including a lip extending substantially parallel to and spaced from an adjacent portion of said body member, said lip of each of said body members being adapted to extend beneath substantially one-half of the full width of the eyelid of the patient with the portion of said body member adjacent said hooked portion covering and shielding the eyelashes and substantially one-half of the full width of the adjacent portion of the eyelid, each of said body members including inner free edges adapted to mate in abutting or overlapping relationship when said eyelash retractor is in position on the eyelid to substantially completely cover and shield the full width of the adjacent portion of the eyelid, to maintain the eyelashes out of the area of the eyeball, and to provide a clear and unobstructed field for examination of and/or surgery on the eyeball.

2. An eyelash retractor according to claim 1 including an enlarged rim connected to and extending around said opposed sides and said outer edge of each of said body members, said enlarged rim providing reinforcing and stiffening so that the general shape of said retractor is retained while each of said body members of thin film material can conform to the shape of the retracted eyelid.

3. An eyelash retractor according to claim 1 wherein said outer edges of the joined together body members define a shallow V-shaped configuration with straight sides joining at a vertex positioned at the juncture of said outer edges.

4. An eyelash retractor according to claim 3 including openings provided in each of said body members and at the juncture of said outer edge with said opposed sides, said openings being adapted to receive a suture thread for holding said eyelash retractor in position in use.

5. An eyelash retractor for covering and shielding the eyelashes and adjacent portion of the eyelid during the examination of and/or surgery on the eyeball of a patient, said eyelash retractor comprising two separate parts with one part being the mirror image of the other part, each of said retractor parts comprising a body member of thin flexible film material including inner and outer edges and outer and inner sides, a hooked portion extending along said inner edge of said body member and including a lip extending substantially parallel to and spaced from an adjacent portion of said body member, said lip being adapted to extend beneath substantially one-half the eyelid of the patient with the portion of said body member adjacent said hooked portion covering and shielding the eyelashes on the corresponding portion of the eyelid to maintain the eyelashes out of the area of the eyeball, and the hooked portion of the other retractor part being adapted to engage the other half of the eyelid of the patient and with the corresponding portion of said body member adjacent said hooked portion covering and shielding the eyelashes on the corresponding portion of the eyelid to maintain the eyelashes out of the area of the eyeball, whereby said two retractor parts are adapted to be positioned in aligned side-by-side relation with said inner sides of said parts being positioned in mating relationship at the intermediate portion of the eyelid of the patient so as to substantially completely cover and shield the eyelashes and substantially the full width of the adjacent portion of the eyelid.

6. An eyelash retractor according to claim 5 including an enlarged rim connected to and extending around said outer edges and said outer sides of each of said retractor parts.

7. An eyelash retractor according to claim 5 wherein said inner edge of each part is joined to the adjacent inner side at an included obtuse angle, such that when the two retractor parts are operatively positioned in side-by-side relation, the two inner edges define a substantially V-shaped configuration.

* * * * *